United States Patent
Pieper (10) Patent No.: US 9,378,308 B2
(45) Date of Patent: Jun. 28, 2016

(54) METHOD AND CLAMPING FIXTURE FOR THE PRODUCING OF A DENTAL DRILLING TEMPLATE

(75) Inventor: Reinhard Pieper, Mannheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 612 days.

(21) Appl. No.: 13/701,233

(22) PCT Filed: Jul. 6, 2011

(86) PCT No.: PCT/EP2011/061353
§ 371 (c)(1),
(2), (4) Date: Feb. 11, 2013

(87) PCT Pub. No.: WO2012/004282
PCT Pub. Date: Jan. 12, 2012

(65) Prior Publication Data
US 2013/0144417 A1    Jun. 6, 2013

(30) Foreign Application Priority Data
Jul. 6, 2010    (DE) .......................... 10 2010 031 018

(51) Int. Cl.
G06F 17/50    (2006.01)
A61C 1/08    (2006.01)
A61C 13/00    (2006.01)
A61C 13/12    (2006.01)

(52) U.S. Cl.
CPC ................ *G06F 17/50* (2013.01); *A61C 1/084* (2013.01); *A61C 13/0004* (2013.01); *A61C 13/12* (2013.01); *A61C 13/0022* (2013.01)

(58) Field of Classification Search
CPC ...... G06F 17/50; A61C 13/12; A61C 3/0004; A61C 1/084; A61C 13/0022
See application file for complete search history.

(56) References Cited

U.S. PATENT DOCUMENTS

| 1,933,718 A | 11/1933 | Devincenzi |
| 5,876,204 A * | 3/1999 | Day et al. ...................... 433/173 |
| 5,927,982 A | 7/1999 | Kruger |

(Continued)

FOREIGN PATENT DOCUMENTS

| DE | 43 28 490 | 3/1995 |
| DE | 43 34 360 | 4/1995 |

(Continued)

OTHER PUBLICATIONS

Handbuch, Herstellung und Anwendung einer individuellen Bohrschablone (Dec. 2007) Straumman GmbH.

*Primary Examiner* — Charles Kasenge
(74) *Attorney, Agent, or Firm* — Fitzpatrick, Cella, Harper & Scinto (57) ABSTRACT

A method for producing a dental drilling template from a blank comprising a pilot borehole and a contact surface using a fabricating device and a virtual 3D drilling template model of the drilling template, said virtual 3D drilling template model comprising a virtual pilot borehole extending along a pilot borehole axis and a virtual contact surface. The method comprises virtually disposing said virtual 3D drilling template model within a 3D blank model of the blank to machine the drilling template from the blank in accordance with the shape and position of said virtual 3D drilling template model within said 3D blank model and applying a mark at a penetration point relevant to said pilot borehole axis on an external surface of said 3D blank model.

13 Claims, 3 Drawing Sheets

(56) References Cited

U.S. PATENT DOCUMENTS

| | | |
|---|---|---|
| 6,319,006 B1 | 11/2001 | Scherer et al. |
| 6,527,550 B1 * | 3/2003 | Hajjar et al. .................... 433/53 |
| 7,125,253 B2 * | 10/2006 | Kitamura et al. ............. 433/173 |
| 7,338,283 B2 * | 3/2008 | Honstein et al. ................ 433/57 |
| 8,043,091 B2 * | 10/2011 | Schmitt ......................... 433/196 |
| 8,808,000 B2 * | 8/2014 | Salcedo et al. .................. 433/75 |
| 2004/0197729 A1 * | 10/2004 | Honstein et al. ................ 433/34 |
| 2005/0281046 A1 | 12/2005 | Lee et al. |
| 2006/0281046 A1 | 12/2006 | Heo |
| 2007/0092854 A1 * | 4/2007 | Powell et al. ................. 433/213 |
| 2009/0136902 A1 * | 5/2009 | Zundorf et al. ............... 433/223 |
| 2009/0253095 A1 * | 10/2009 | Salcedo et al. .................. 433/75 |
| 2009/0274990 A1 | 11/2009 | Kim |
| 2009/0298008 A1 * | 12/2009 | Groscurth et al. .............. 433/74 |
| 2010/0082148 A1 | 4/2010 | Cinader, Jr. |
| 2010/0105008 A1 * | 4/2010 | Powell et al. .............. 433/202.1 |
| 2011/0018184 A1 | 1/2011 | Steger |
| 2011/0111364 A1 * | 5/2011 | Haber ............................. 433/72 |
| 2011/0111371 A1 * | 5/2011 | Haber ........................ 433/201.1 |

FOREIGN PATENT DOCUMENTS

| | | |
|---|---|---|
| DE | 196 29 708 | 2/1998 |
| DE | 298 17 575 | 2/1999 |
| DE | 199 52 962 | 5/2001 |
| DE | 10 2005 040 739 | 3/2007 |
| EP | 2 072 018 | 6/2009 |
| FR | 2 446 629 | 8/1980 |
| WO | 99/32045 | 7/1999 |
| WO | 2009/100863 | 8/2009 |
| WO | 2011/091382 | 7/2011 |

* cited by examiner

METHOD AND CLAMPING FIXTURE FOR THE PRODUCING OF A DENTAL DRILLING TEMPLATE

The invention relates to a method for the producing of a dental drilling template comprising a pilot borehole and a contact surface, there being present a virtual 3D model of the drilling template, comprising a virtual pilot borehole extending along a pilot borehole axis, and comprising a virtual contact surface.

PRIOR ART

A number of methods and devices for the producing of a drilling template comprising a pilot borehole for the accommodation of a dental implant are known from the prior art.

The brochure "Herstellung and Anwendung einer individuellen Bohrschablone" [Producing and use of an individual drilling template] issued by Straumann GmbH discloses a method for the producing of a drilling template. The first step comprises making a situation cast of plaster. In a second step, a resin template is vacuum-formed over the situation cast. In a third step, a second plaster cast is made, which is sawed to present a view of the planned implant position, and the measured bone profile is transferred thereto and an implant axis set. In the fourth step, a wax-up of the planned restoration is produced on the original situation cast. In a fifth step, a duplicate of the wax-up cast is made and a resin template is vacuum-formed over the same. In a sixth step, the new resin template is transferred to the situation cast. In a seventh step, the ascertained implant position and the implant axis are marked on the situation cast, and a borehole is drilled along the implant axis by means of a parallelometer equipped with a pilot drill. In an eighth step, a titanium pin is inserted into the borehole. In a ninth step, a new resin template is vacuum-formed over the titanium pin inserted in the cast. In a tenth step, the resin template is removed from the cast, and the titanium pin is replaced by a shorter titanium pin. In an eleventh step, the resin template is placed on the previously fabricated cast with the bone profile drawn in, and the implant axis is checked. The position and direction of the borehole can still be corrected if necessary. In a twelfth step, a stepped titanium pin is placed in the borehole, and any undercuts are blocked with plaster, wax or resin. A new resin template is vacuum-formed over the stepped titanium pin. Following the removal of the stepped titanium pin, an occlusal opening is cut or ground in the resin template, and a drill sleeve with collar is inserted into the resin template. The resin template is then ground or cut in the region of the implantation site. Alternatively, a drill sleeve can be placed over the titanium pin, in the ninth step, and the drill sleeve can be fixed with resin or plaster. Then a resin template is vacuum-formed over the drill sleeve, and the borehole opening is exposed by grinding for the purpose of receiving the pilot drill.

DE 199 52 962 A1 discloses a method for the production of a drilling aid for a dental implant, for which purpose an X-ray image of the jaw is first produced and a three-dimensional optical scan of the visible surface of the jaw and teeth is then carried out. The measured data records from the X-ray image and the three-dimensional optically scanned measurements are correlated. Based on the information available, such as the type and position of the implant relative to the adjacent teeth, a template that rests on the adjacent teeth is planned and produced, and thus precise drilling of the implant pilot borehole is made possible. Based on the X-ray data, the implant can be predetermined and positioned in ways that are known in the prior art. Based on ascertained information concerning the surface structure, i.e., the occlusal surfaces of adjacent teeth, it is possible to grind out an implantation aid in the form of a drilling template by implementation of a CAD/CAM unit. Using the measured data, a CAD/CAM machine is able to fabricate the drilling template comprising the negative of the occlusal surfaces and a guide path for the drill. A stop member that defines the depth of the borehole is then provided on the drilling template.

WO 99/32045 discloses a method for the producing of a dental drilling aid for implants. Firstly, using an image of the jaw, a three-dimensional computer image is modeled based on an impression surface. Then the position and the depth of the boreholes are ascertained, and a set of implant borehole coordinates is fed to a computer-controlled fabricating machine. By means of a precision machine tool, a drill guiding mans is prepared inside the body to be drilled for each of the previously entered sets of borehole coordinates, which drill guiding means has a borehole position and borehole orientation ascertained from the relevant portion of the jaw.

A disadvantage of this method is that most CAD/CAM machines have limited degrees of freedom, and it is not possible to drill, in particular, boreholes disposed obliquely in relation to each other. Therefore, the producing of drilling templates by means of a CAD/CAM machine is possible only for limited therapeutic areas. In most cases, the drilling template is fabricated either individually in the laboratory or at a central location in accordance with prior CAD/CAM planning, for example using a hexapod designed to allow for a maneuverability of the object to be machined in all six degrees of freedom and by means of a parallelometer for drilling vertical boreholes. Usually, CT-DVT templates, bite plates, and jaw models made of plaster are used for the central producing of drilling jigs. These are mounted on the elaborately designed hexapod and adjusted with the aid of a number of measured points. This procedure is very elaborate and thus error-prone.

It is therefore an object of this invention to provide a method and a device that make it possible to fabricate any type of drilling template comprising oblique drilling axes using a conventional fabricating machine having a limited number of degrees of freedom.

SUMMARY OF THE INVENTION

The object of the invention is a method for the producing of a dental drilling template from a blank, which dental drilling template comprises a pilot borehole and a contact surface, there being present a virtual 3D model of the drilling template comprising a virtual pilot borehole extending along a pilot borehole axis and a virtual contact surface. In one method step, the virtual 3D drilling template model is positioned inside a 3D model of the blank in a virtual environment in order to carve the drilling template from the blank according to the shape and position of the virtual 3D drilling template model positioned within the 3D blank model. In a further method step, a penetration point relevant to the pilot borehole axis is predetermined on an external surface of the 3D blank model by virtual computerization before the drilling template is carved from the blank. Then a mark is applied to the external surface of the blank at the penetration point relevant to the pilot borehole axis. According to an alternative method, first a penetration point relevant to the pilot borehole axis is predetermined on an external surface of the virtual 3D drilling template model, and then a mark is applied to the external surface of the drilling template at the penetration point during or after the operation of carving the drilling template from the blank.

The dental drilling template to be fabricated can be any desired type of drilling template such as one supported by the adjacent teeth for minimally invasive surgery or a drilling template supported by the jaw bone for so-called "open flap" surgery. The drilling template can be fabricated for the purpose of drilling pilot boreholes and for the insertion of insert sleeves.

The pilot borehole serves to guide a drill for the purpose of drilling the planned implant borehole, as computed during implant planning, for the insertion of an implant. The drill used can be a so-called pilot drill. Alternatively, the pilot borehole can be configured such that a drill sleeve can be inserted into the pilot borehole, the internal surface of said drill sleeve serving to guide the drill. During planning of an implant, an X-ray image of the jaw and a three-dimensional optical scan of the visible surface of the jaw and teeth can be used in order to determine, in a virtual environment, the type and position of the implant relative to the jaw. In particular, the precise position, the angle relative to the jaw, and the depth of the individual boreholes are planned for the insertion of the implants. Based on the implant boreholes to be drilled, a virtual 3D model of the drilling template is then planned that comprises virtual pilot boreholes and a virtual contact surface, which is preferably shaped as a negative counterpart of the surface of the adjacent teeth.

The planned 3D model of the drilling template is the starting point for the present method of the invention. In a first step, the virtual 3D drilling template model is positioned inside the 3D model of a blank in a virtual environment. This can be effected by means of a computer comprising a monitor and a mouse, and the user can use virtual tools for rotating and moving the 3D drilling template model located within the 3D blank model. Following positioning of the 3D drilling template model, the position data can be stored. In a next step, the drilling template is carved from the blank, as planned for the virtual 3D drilling template model within the 3D blank model. For this purpose, a blank made of ceramics or plastics material may be used whose dimensions are large enough to enable the drilling template to be carved therefrom. The blank can be dimensionally of any desired geometric shape and does not include any patient-related elements, such as an impression of the patient's teeth. The drilling template is carved by means of a fabricating device, which may be a conventional CAD/CAM device having limited degrees of freedom. Prior to the operation of carving the drilling template and following positioning of the 3D drilling template model within the 3D blank model, one or more penetration points relevant to the pilot borehole axis are predetermined on the external surface of the 3D blank model, i.e. on the external surface of the virtual 3D drilling template model, by virtual computerization. This can be carried out automatically with the aid of a computer in that the user activates this function, for example by means of a virtual switch, at the conclusion of the planning procedure.

The position data relating to the penetration points relative to the blank can be stored and forwarded to the fabricating device. In a further step, one or more marks are applied to one or more penetration points relevant to the pilot borehole axis either on the external surface of the blank or the external surface of the drilling template. If, according to a first exemplary embodiment, the boreholes are drilled first and the drilling template is only then carved from the blank, the marks are applied to the external surface of the blank. When, according to the second exemplary embodiment of the method, the drilling template is first carved from the blank and the pilot boreholes are subsequently drilled, the marks are applied to the external surface of the drilling template. The marks can be of any desired form.

The advantage of the method of the invention is that the boreholes are drilled, as planned, in a drilling jig that is separate from the fabricating device. The drilling jig can be a conventional parallelometer. The planned pilot boreholes are drilled at the marks by means of the drilling jig in that either the blank or the finished drilling template is clamped in the drilling jig such that the axis of a drill in the drilling jig coincides with the planned pilot borehole axis between the two marks.

Thus the method of the invention makes it possible to fabricate a drilling template in a simple and quick manner by means of any desired conventional fabricating device and a drilling jig located on the dentist's premises. This obviates the necessity to fabricate the drilling template on the basis of planning data in a central laboratory.

Advantageously, the blank can be clamped and scanned in a fabricating device before the drilling template is carved therefrom.

The position and orientation of the blank relative to the fabricating device is predetermined by scanning the blank clamped in the fabricating device, whereupon a tool pertaining to the fabricating device, such as a milling tool, is controlled in a further step such that the external surface of the drilling template is milled out of the clamped blank according to the planning data.

Advantageously, the planned pilot borehole can be drilled before the drilling template is carved from the blank. Before the drilling template is carved from the blank, a penetration point relevant to the pilot borehole axis can be predetermined on an external surface of the 3D blank model by virtual computerization. In a next step, the blank can be clamped and scanned in the fabricating device. A mark is then applied to the external surface of the blank at the penetration point relevant to the pilot borehole axis. The blank is removed from the fabricating device. Then the marked blank is clamped in a clamping fixture and held in place by means of a securing device. The clamping fixture is then removed, and the planned pilot borehole is drilled at the position of the mark by means of a drilling jig.

In this embodiment of the method, the pilot borehole is first drilled in the blank, and the drilling template is then carved from the blank only in the second step so that the pilot borehole is disposed at the planned location in the drilling template and has the planned orientation. A number of pilot boreholes may be drilled, if desired. If this is the case, the steps of clamping the blank in the clamping fixture, holding it in place by means of the securing device, removing the blank from the clamping fixture, and drilling the pilot borehole by means of the drilling jig will have to be repeated for each of the pilot boreholes.

Advantageously, the mark can be applied at the penetration point relevant to the pilot borehole axis in the form of an indentation produced by the fabricating device.

The mark can be applied in the form of an indentation. This facilitates clamping of the blank in the clamping fixture.

Advantageously, the clamping fixture can comprise two mandril tips, and two marks can be applied to the blank at the two penetration points relevant to the pilot borehole axis. The marked blank is then clamped at the two marks between the mandril tips in the clamping fixture.

Thus the blank is clamped, as planned, in a precise position in the clamping fixture for the purpose of drilling the planned pilot borehole. The indentations on the blank can be in the form of a counterpart of the two mandril tips. This makes it possible to clamp the blank with positional accuracy.

Advantageously, the planned pilot borehole can be drilled after the drilling template has been carved from the blank. When the drilling template is being carved from the blank, a mark is applied to a surface of the drilling template, while a blank holder remains firmly attached to the drilling template. The drilling template is removed from the fabricating device together with the blank holder. The drilling template is clamped in a clamping fixture, and the blank is held in place by means of a securing device. The clamping fixture is removed. The planned pilot borehole is then drilled at the mark by means of a drilling jig.

In this alternative embodiment of the method, the drilling template is carved from the blank in the first step, while the planned pilot borehole is drilled in the second step. When a number of pilot boreholes are to be drilled, the steps of clamping the drilling template in the clamping fixture, holding the blank in place by means of the securing device, and drilling the pilot borehole by means of the drilling jig are repeated for each pilot borehole. Thus the drilling template can be handled more simply than a blank of larger dimensions during the process of drilling the pilot boreholes.

Advantageously, the mark can be applied to the surface of the drilling template in the form of an indentation by means of the fabricating device.

The marks in the form of indentations on the surface of the drilling template make it possible to clamp the drilling template in a precise position, as planned, for the purpose of drilling the planned pilot borehole.

Advantageously, the clamping fixture can comprise two mandril tips, and two marks can be applied to the drilling template at the two penetration points relevant to the pilot borehole axis, whereupon the marked drilling template is clamped between the mandril tips in the clamping fixture at the two marks.

This makes it possible to position the marked drilling template precisely in the clamping fixture. The marks in the form of indentations can be counterparts of the two mandril tips.

Advantageously, the securing device can comprise rubber pads, between which the blank can be clamped.

This makes it possible to hold the blank securely in place in the clamping fixture for the purpose of drilling the planned pilot borehole.

Advantageously, the planned pilot borehole can be drilled before the drilling template is carved from the blank, and a penetration point relevant to the pilot borehole axis is predetermined on an external surface of the 3D blank model by virtual computerization before the drilling template is carved from the blank, and the blank is clamped and scanned in the fabricating device. A mark is applied to the external surface of the blank at the penetration point relevant to the pilot borehole axis. Then the blank is removed from the fabricating device. The marked blank attached to a blank holder is clamped in a clamping fixture. The clamping fixture comprises adjusting means for adjusting a tilt angle and a rotary angle of the blank relatively to the clamping fixture. The tilt angle and rotary angle are then set by said adjusting means such that the blank is then positioned with the planned pilot borehole axis coinciding with an axis of a tool of a drilling jig for drilling the planned pilot borehole. The planned pilot borehole is drilled at the mark by means of the drilling jig.

In this alternative method, use is made of a clamping fixture comprising adjusting means for adjusting a tilt angle and a rotary angle of the blank. This renders unnecessary the method step of fixing and removing the clamping fixture before the drilling process is carried out using the drilling jig. During the procedure of planning the pilot borehole, distinct tilt angles and rotary angles are computed for each of the pilot boreholes. The tilt angle and rotary angle of the clamped blank are then set accordingly by the adjusting means. The clamping fixture can then be moved to a position below the drilling jig such that the axis of the tool, such as a drill or a milling tool, coincides with the pilot borehole axis. Thus the planned borehole is precisely drilled through the blank without necessitating the use of a securing device.

Advantageously, the planned pilot borehole can be drilled after the drilling template has been carved from the blank, with a penetration point relevant to the pilot borehole axis being predetermined on an external surface of the 3D drilling template model by virtual computerization before the drilling template is carved from the blank. The blank is then clamped and scanned in the fabricating device and a mark applied to a surface of the drilling template at the penetration point during the operation of carving the drilling template from the blank. A blank holder remains firmly attached to the drilling template. The drilling template is removed from the fabricating device together with the blank holder. The marked drilling template is then clamped in a clamping fixture by way of the blank holder. The clamping fixture comprises adjusting means for setting the tilt angle and the rotary angle of the blank relatively to the clamping fixture, and the tilt angle and rotary angle are set using said adjusting means such that the blank is positioned with the planned pilot borehole axis coinciding with an axis of a tool of a drilling jig for the purpose of drilling the planned pilot borehole. The planned pilot borehole is then drilled at the mark by means of the drilling jig.

In this alternative method, use is made of the same clamping fixture as in the previous method, comprising adjusting means for setting the tilt angle and the rotary angle. The difference is that the drilling template is first carved from the blank, while the marked drilling template is subsequently clamped in the clamping fixture. The adjusting means are adjusted to set the computed tilt angle and the computed rotary angle for each of the pilot boreholes, and the clamping fixture is moved to a position below the drilling jig such that the axis of the drilling tool coincides with the pilot borehole axis, and the pilot borehole is then drilled at the mark. The blank holder is provided with a pin that is adapted to engage a groove on the holding fixture for the blank such that it is secured against rotation.

Advantageously, the adjusting means allow for adjustment of a tilt angle in the range of from 0° to 90° and for adjustment of a rotary angle in the range of from 0° to 360°.

This makes it possible to drill any pilot borehole of any desired orientation.

Advantageously, several marks can be applied to the blank, or to the drilling template, by means of the fabricating device, and each pilot borehole can be provided with a distinct number.

The numbering of each of the planned pilot boreholes makes it easier for the user to select a suitable computed tilt angle and rotary angle for the pilot borehole to be drilled so as to avoid the production of erroneously drilled boreholes.

Advantageously, the drilling template comprises a stop member in the pilot borehole that serves to limit the depth of the borehole to be drilled. The stop member is carved from the blank as part of the drilling template.

Thus the stop member that determines the depth of each of the boreholes to be drilled can be fabricated along with the drilling template automatically by the fabricating device with the aid of a computer.

A further object of the invention is a clamping fixture for clamping a blank for the purpose of fabricating a drilling template, which clamping fixture comprises a base, a first adjusting means for setting a tilt angle of the blank and a second adjusting means for setting a rotary angle of the blank. The blank is capable of being positioned relatively to the clamping fixture using said two adjusting means for the tilt angle and rotary angle such that a planned pilot borehole axis coincides with the axis of a tool of a drilling jig used for drilling a pilot borehole.

Thus the method of the invention can also be carried out by means of this clamping fixture without the use of a securing device. In a first step, the tilt angle and the rotary angle for each borehole are set and fixed by the adjusting means, and then, in the second step, the base is moved to a position below the drilling jig such that the axis of the tool coincides with the axis of the pilot borehole. The borehole is then drilled. These steps are repeated for each of the boreholes.

Advantageously, the clamping fixture can additionally comprise a rotatable arm, a tilt scale for reading off the tilt angle, a rotary scale for reading off the rotary angle, a holding fixture for the blank holder for securing the blank, a means for holding the blank holder in place, a first nut for securing the rotary angle, a second nut for securing the tilt angle, the holding fixture being in the form of a counterpart of the blank holder.

The rotary arm on which the blank is mounted makes it possible to set the tilt angle, which can be read off from the tilt scale. The blank holder is held in place in the holding fixture non-rotatably attached to the rotatable arm for the purpose of setting the rotary angle. The rotary angle can be read off from the rotary scale. Once the tilt angle and the rotary angle have been set, said angles are secured by means of a first and a second nut. The blank holder comprises a pin that engages a groove on the holding fixture for the blank holder for the purpose of holding the blank in place to secure it against rotation.

Advantageously, the adjusting means allow for setting of a tilt angle in the range of from 0° to 90° and for setting the rotary angle in the range of from 0° to 360°.

This enables the blank to be positioned precisely for each pilot borehole.

BRIEF DESCRIPTION OF THE DRAWINGS

Exemplary embodiments of the invention are shown in the drawings, in which.

EXEMPLARY EMBODIMENTS

Figure 1:
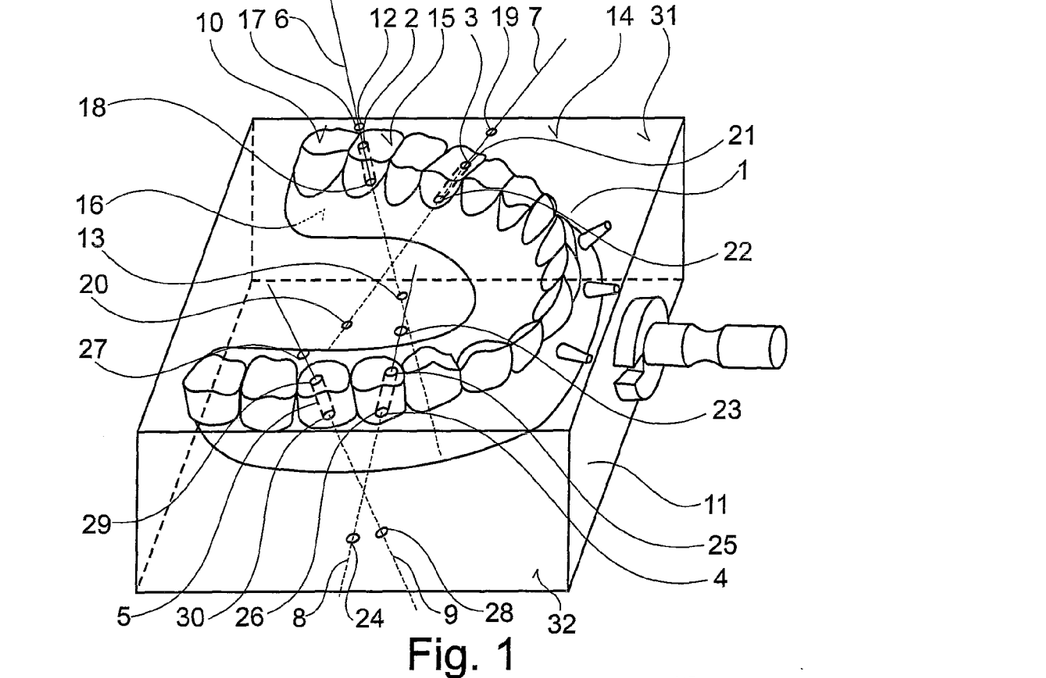
FIG. 1 is a diagrammatical representation of a virtual 3D drilling template model.

FIG. 1 is a diagrammatical representation of a virtual 3D drilling template model 1 comprising four pilot boreholes 2, 3, 4, 5 extending along the pilot borehole axes 6, 7, 8, and 9, and the 3D drilling template model comprises a virtual contact surface 10 that corresponds to the shape of the teeth and a portion of the gums. The virtual 3D drilling template model is virtually disposed within a 3D blank model 11. The virtual positioning of the 3D drilling template model can be effected automatically by computerization or by a user implementing a computer monitor and a mouse or keyboard. Once the position of the 3D drilling template model within the 3D blank model has been finally predetermined, the penetration points 12 and 13 relevant to the pilot borehole axis 6 are predetermined on a virtual external surface 14 of the 3D blank model 11. Penetration points 17 and 18 are also predetermined on the two external surfaces 15 and 16 of the 3D drilling template model 1. Accordingly, penetration points 19 and 20 relating to the pilot borehole axis 7 are predetermined on the external surface 14 of the 3D blank model, and penetration points 21 and 22 are predetermined on the two external surfaces 15 and 16 of the 3D drilling template model. The penetration points 23 and 24 relevant to the pilot borehole axis 8 are predetermined on the external surface 14 and its penetration points 25 and 26 are predetermined on the external surfaces 15 and 16. The penetration points 27 and 28 of the fourth pilot borehole axis 9 are predetermined on the external surface 14 and the penetration points 29 and 30 are predetermined on the two external surfaces 15 and 16. The penetration points can be automatically predetermined by computerization, since the position of the 3D drilling template model within the 3D blank model and the pilot borehole axes 6, 7, 8, and 9 are known.

Figure 2:
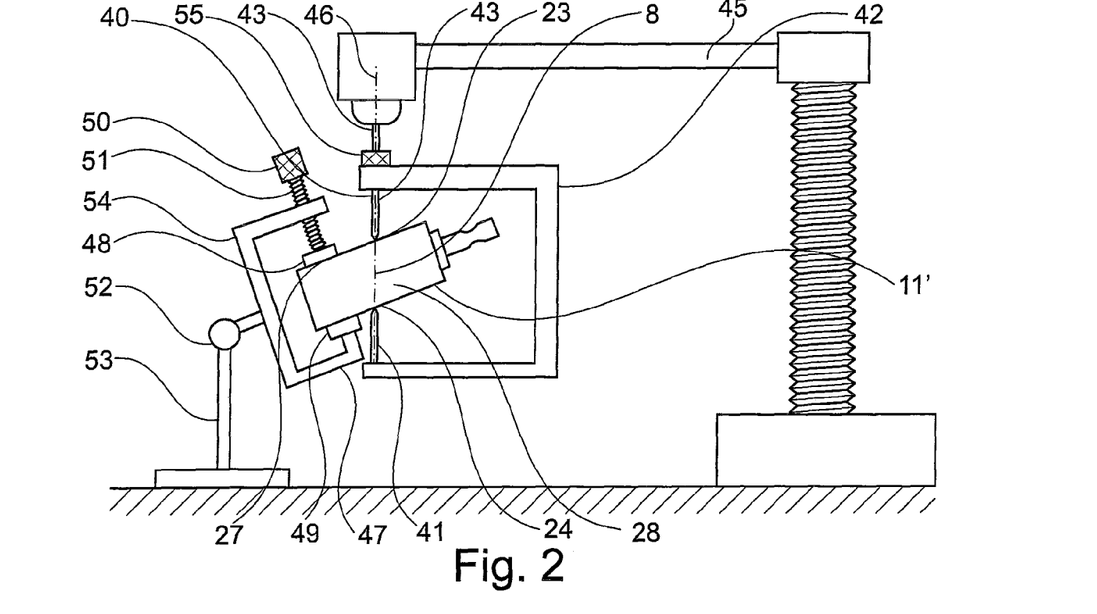
FIG. 2 is a diagrammatical representation of a blank clamped in a clamping fixture.
Figure 3:
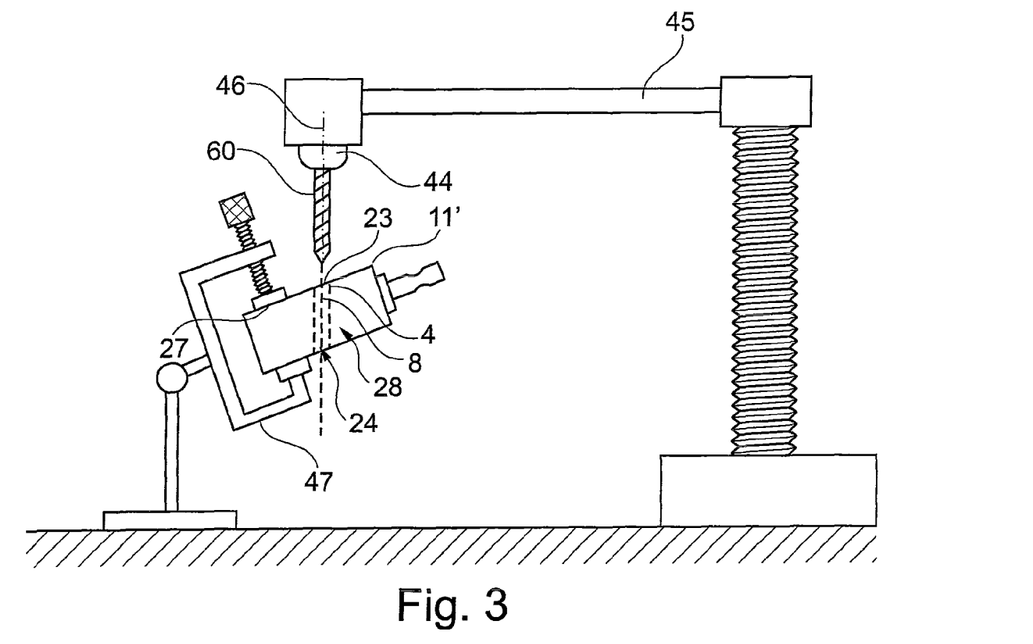
FIG. 3 is a diagrammatical representation of a blank and a drilling jig for drilling the planned pilot borehole.
Figure 4:
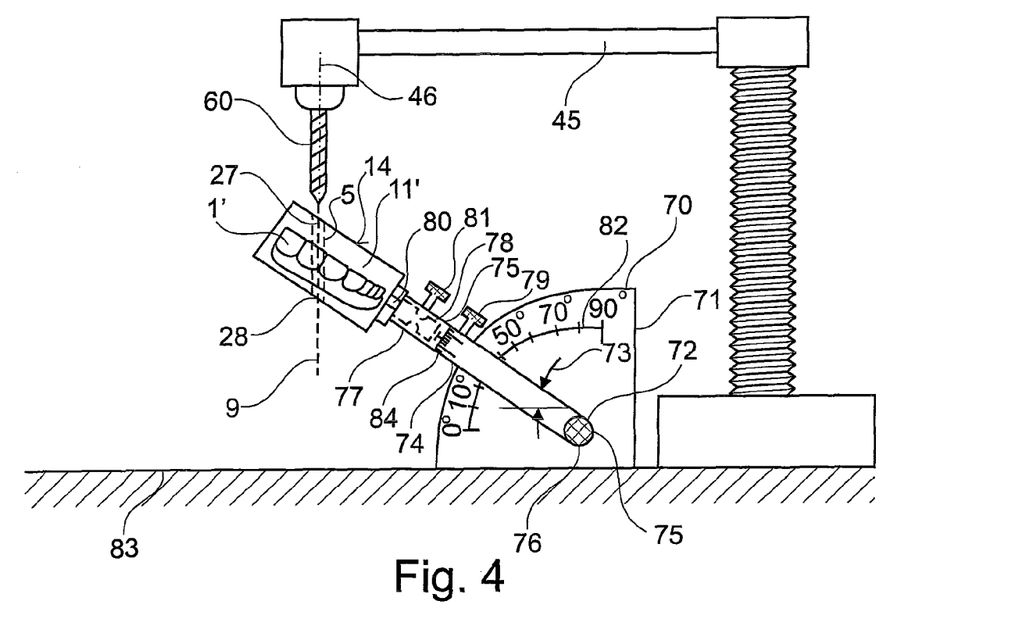
FIG. 4 is a diagrammatical representation of a blank clamped in an alternative clamping fixture.
Figure 5:
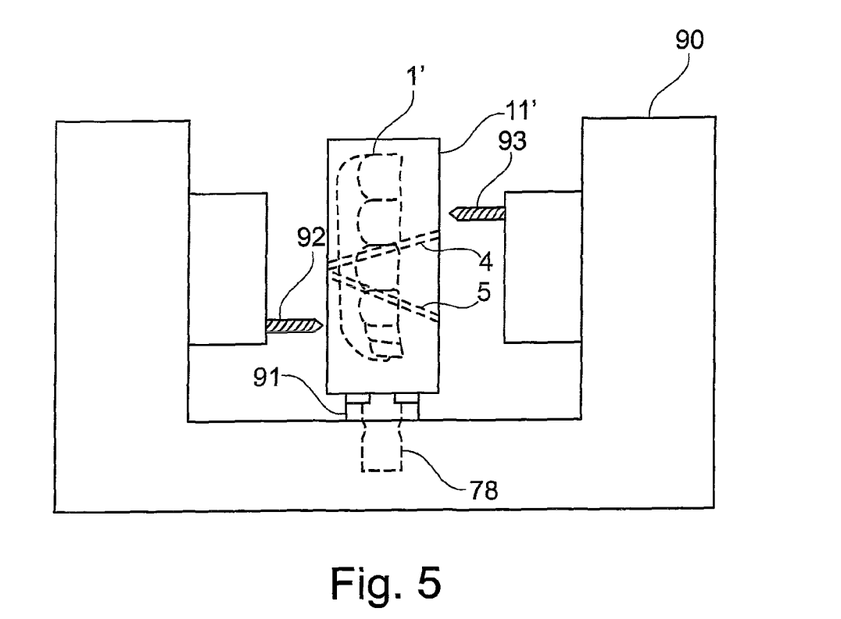
FIG. 5 is a diagrammatical representation of a fabricating device with the blank provided with pilot boreholes.
Figure 6:
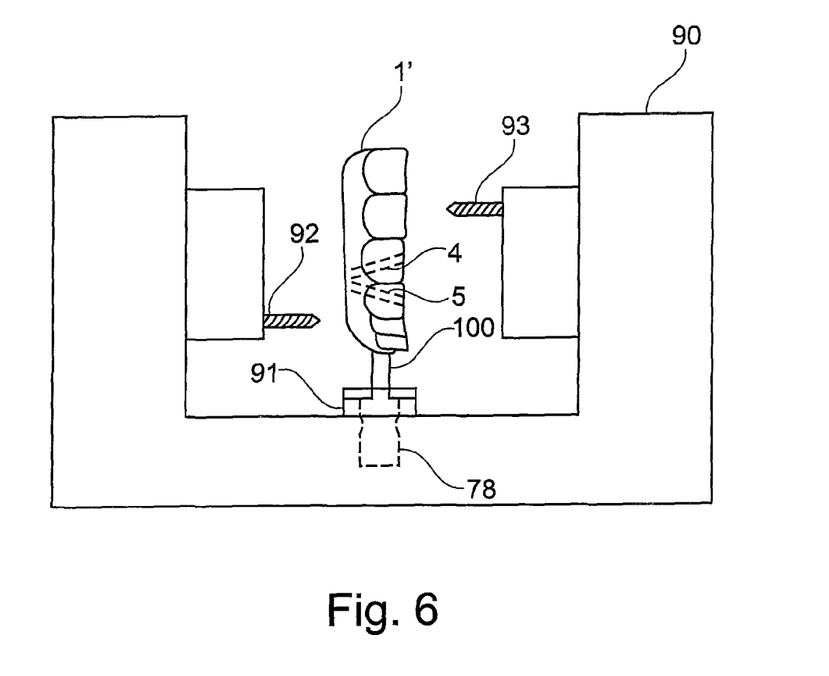
FIG. 6 is a diagrammatical representation of the fabricating device after the drilling template has been carved from the clamped blank.

In a first embodiment of the method of the invention, marks are applied to the top side 31 of the external surface 14 at the penetration points 12, 19, 23, and 27 and to the underside 32 of the external surface 14 at penetration points 13, 20, 28, and 24, in a first step, using a fabricating device as shown in FIGS. 5 and 6. In the second step, the blank is clamped, as shown in FIG. 2, in a clamping fixture and held in place by means of a securing device. In a third step, pilot boreholes are drilled at the marks, as planned, by means of a drilling jig, as shown in FIGS. 3 and 4. In a fourth step, the blank comprising the pilot boreholes is re-clamped in the fabricating device, as shown in FIGS. 5 and 6, and the drilling template is carved from the blank in accordance with the planned shape and position of the virtual 3D drilling template model 1 within the 3D blank model 11.

According to a second, alternative embodiment of the method of the invention, the drilling template 1' is first carved from the blank 11' by means of the fabricating device shown in FIGS. 5 and 6, with marks applied, in the form of indentations, to the top external surface 15 of the drilling template 1' at the penetration points 17, 21, 25, and 29 and to the bottom external surface 16 of the drilling template 1' at the penetration points 18, 22, 26, and 30. In a second step, the drilling template 1' is clamped between the marks in the clamping fixture shown in FIG. 2 and held in place by means of the securing device. In a third step, pilot boreholes are drilled, as shown in FIG. 3, at the marks on the drilling template, the marked drilling template 1' being clamped instead of the blank 11'. Instead of the clamping fixture and securing device shown in FIGS. 2 and 3, the alternative clamping fixture shown in FIG. 4 can be used for positioning the marked drilling template. The pilot boreholes are then drilled, as planned, at the marks provided on the drilling template.

FIG. 2 is a diagrammatical representation of a blank 11' that has been provided with marks in the form of conical indentations at the penetration points 27, 28, 23, and 24 by means of the fabricating device shown in FIGS. 5 and 6. The other marks at the penetration points 12, 19, 20, and 13 are not shown in the figure. The blank 11' is clamped at the marks 23 and 24 between two mandril points 40 and 41 of a clamping fixture 42. The distance between the two mandril points 40 and 41 can be altered by displacing the top mandril point 40 and can be secured by means of a lock nut 55. The top mandril point 40 pertains to a long mandril 43 clamped in a chuck 44 of a drilling jig 45. The drilling jig 45 can be a conventional parallel milling machine (parallelometer) that is suitable for drilling vertical boreholes. Due to the fact that the mandril 43 is clamped in the chuck 44, the planned pilot borehole axis 8 coincides with a drilling axis 46 of the tool in the drilling jig 45 to be used. The blank 11' is held in place by means of a securing device 47. The securing device 47 comprises rubber pads 48 and 49 that are resilient and clamp the blank 11' on both sides, as in the case of a bar clamp, by means of a knob 50 and a screw 51. The securing device comprises a ball-and-socket joint 52 and a stand 53 adapted to adjust the position of a movable clamping bar 54 in a desired manner.

FIG. 3 shows the setup for a method step that follows the one illustrated in FIG. 2. The clamping fixture 42 shown in FIG. 2 is removed from the chuck 44 and replaced by a tool, namely a drill 60, and the blank 11' is held in place by means of the securing device 47 such that the drilling axis 46 of the tool 60 coincides with the planned pilot borehole axis 8. The planned pilot borehole 4 extending between the marks 23 and 24 is drilled by means of the tool 60. The other planned pilot boreholes 2, 3, and 5 are drilled in the same way by repeating the steps illustrated in FIGS. 2 and 3, namely by clamping the blank in the clamping fixture 42, holding the blank 11' in place by means of the securing device 47, and drilling the boreholes by means of the drilling jig 45 between the marks on the external surfaces of the blank 11', as shown in FIG. 3. According to an alternative method, the drilling template 1' can be carved from the blank first, with marks 17, 18, 21, 22, 25, 26, 29, and 30 being applied in the form of indentations to the external surfaces 15 and 16 of the drilling template by means of the fabricating device shown in FIGS. 5 and 6. Then the marked drilling template 1' is clamped, as shown in FIGS. 2 and 3, in the clamping fixture 42 between the respective marks relevant to a borehole and held in place by means of the securing device 47, after which the planned borehole is drilled by means of the drilling jig.

FIG. 4 shows an alternative clamping fixture 70 comprising a base 71, a first adjusting means 72 for adjusting a tilt angle 73, namely a tiltable arm 74 that can pivot about an axis 75 and that can be held in position by a lock nut 76. The clamping fixture 70 comprises a second adjusting means for adjusting the rotary angle, which is indicated on the rotary scale 84, which adjusting means 75 comprises a holding fixture 77 for accommodating the blank holder 78, which holding fixture 77 is adapted to be rotatable forming an extension of the rotatable arm 74, and the rotary angle can be set by means of a second setscrew 79. The holding fixture 77 comprises a pin 80 that engages a groove on the blank holder 78 so as to secure the blank against rotation. The blank holder 78 is secured in the holding fixture 77 by means of a third lock nut 81. The tilt angle is indicated on the tilt scale 82. The base 71 is freely movable on the subsurface 83. According to the method of the invention, a specific tilt angle and a specific rotary angle are computed for each pilot borehole during the planning process. In FIG. 4, the corresponding tilt angle and the corresponding rotary angle for the pilot borehole 5 between the external marks 27 and 28 on the external surface 14 of the blank 11' have been set. Then the base 71 was moved on the subsurface 83 such that the tool 60 of the drilling jig 45 aligned with the mark 27. Then the planned hole 5 was drilled by means of the tool 60. Within the blank 11', there is shown the planned drilling template 1', which is carved from the blank, as shown in FIGS. 5 and 6, by means of the fabricating device shown in FIGS. 5 and 6, only after all of the pilot boreholes 2, 3, 4, 5 have been drilled. In order to drill the other pilot boreholes 2, 3, 4, the method steps listed above must be repeated, namely, setting the computed tilt angle 73 and the rotary angle, moving the base 71 so that the axis 46 of the tool 60 coincides with the axis 9 of the planned pilot borehole 5, and drilling the borehole by means of the tool 60. The clamping fixture shown in FIG. 4 can also be used for the alternative method of the invention, in which the drilling template 1' is carved in a first step by means of the fabricating device shown in FIGS. 5 and 6, with the top and bottom external surfaces 15 and 16 of the drilling template being provided with marks in the form of indentations, while the pilot boreholes are not drilled on the marked drilling template before the second step. To this end, the drilling template remaining attached to the blank holder 78, as shown in FIG. 6, is clamped in the holding fixture 77, and the base 71 is moved such that the tool 60 is positioned to align with the appropriate top mark. Then the planned pilot borehole is drilled by means of the tool 60. The first adjusting means 72 and the second adjusting means 75 are adapted to allow for adjustment of a tilt angle in the range of from 0° to 90° and a rotary angle in the range of from 0° to 360°.

FIG. 5 is a diagrammatical representation of a fabricating device 90, in which the blank 11' is clamped by means of the blank holder 78 in a socket 91. The planned drilling template 1' is carved in accordance with the 3D drilling template model 1 shown in FIG. 1 using the milling tools 92 and 93, the fabricating device being controlled accordingly by a computer. The blank 11' comprising the drilled pilot boreholes 4 and 5 is shown in FIG. 5, which pilot boreholes 4 and 5 are drilled according to the first method illustrated in FIGS. 2 and 3 or the second, alternative method illustrated in FIG. 4.

FIG. 6 shows the finished drilling template 1' comprising the drilled pilot boreholes 4 and 5 after the drilling template has been carved from the blank. The drilling template 1' remains attached to the blank holder 78 by means of a connecting pin 100 that can be subsequently manually ground off from the drilling template 1'.

In the alternative method of the invention, the drilling template 1' comprising marks at the penetration points for the pilot borehole axes is carved from the blank 11' in a first step, for which purpose the drilling template 1' remains attached to the blank holder 78 by means of the connecting pin. Only in the second step is the marked drilling template, which is attached to the blank holder 78, clamped in the clamping fixture shown in FIG. 2 or FIG. 4, after which the pilot boreholes are drilled, as described above.

LIST OF REFERENCE NUMERALS OR CHARACTERS 1 3D drilling template model
1' drilling template
2 pilot borehole
3 pilot borehole
4 pilot borehole
5 pilot borehole
6 pilot borehole axis
7 pilot borehole axis
8 pilot borehole axis
9 pilot borehole axis
10 contact surface
11 3D blank model
11' blank
12 penetration point
13 penetration point
14 external surface
15 external surface
16 external surface 17 penetration point
18 penetration point
19 penetration point
20 penetration point
21 penetration point
22 penetration point
23 penetration point
24 penetration point
25 penetration point
26 penetration point
27 penetration point/mark
28 penetration point/mark
29 penetration point
30 penetration point
31 top surface
32 bottom surface
40 mandril point
41 mandril point
42 clamping fixture
43 mandril
44 chuck
45 drilling jig
46 drilling axis
47 securing device
48 rubber pad
49 rubber pad
50 handle
51 setscrew
52 ball-and-socket joint
53 stand
54 clamping rail
55 locknut
60 drill/tool
70 clamping fixture
71 base
72 adjusting means
73 tilt angle
74 rotatable arm
75 axis/adjusting means
76 locknut
77 holding fixture
78 blank holder
79 setscrew
80 pin
81 locknut
82 tilt scale
83 subsurface
84 rotary scale
90 fabricating device
91 socket
92 milling cutters
93 milling cutters
100 connecting pin

The invention claimed is:

1. A method for producing a dental drilling template from a blank comprising a pilot borehole and a contact surface using a fabricating device and a virtual 3D drilling template model of said drilling template, said virtual 3D drilling template model comprising a virtual pilot borehole extending along a pilot borehole axis and a virtual contact surface, comprising the steps of:
   virtually disposing said virtual 3D drilling template model within a 3D blank model of said blank, in order to machine said drilling template from said blank in accordance with a shape and position of said virtual 3D drilling template model within said 3D blank model; and
   (i) prior to carving said drilling template from said blank, predetermining a penetration point relevant to said pilot borehole axis by virtual computerization on an external surface of said 3D blank model and applying a mark to an external surface of said blank at said penetration point relevant to said pilot borehole axis, wherein said mark is applied at said penetration point relevant to said pilot borehole axis as an indentation using said fabricating device, or
   (ii) predetermining a penetration point relevant to said pilot borehole axis on an external surface of said virtual 3D drilling template model and, during or after said carving of said drilling template from said blank, applying a mark to an external surface of said drilling template at said penetration point relevant to said pilot borehole axis using said fabricating device,
   wherein said drilling template comprises a stop member at said pilot borehole restricting a depth of said pilot borehole to be drilled, said stop member being carved from said blank as part of said drilling template.

2. A method as defined in claim 1, wherein prior to carving said drilling template, said blank is clamped in said fabricating device and scanned.

3. A method as defined in claim 1 or 2, further comprising:
   producing said pilot borehole prior to carving said drilling template from said blank;
   predetermining said penetration point relevant to said pilot borehole axis on an external surface of said 3D blank model by virtual computerization prior to carving said drilling template from said blank;
   clamping and scanning said blank in said fabricating device;
   applying said mark to said external surface of said blank at said penetration point relevant to said pilot borehole axis;
   removing said blank from said fabricating device;
   clamping said marked blank in a clamping fixture, said blank being held in position using a securing device;
   removing said clamping fixture; and
   drilling said pilot borehole at said mark using a drilling rig.

4. A method as defined in claim 3, wherein said clamping fixture comprises two mandril points and two marks are applied to said blank at said two penetration points relevant to said pilot borehole, said marked blank being clamped between said mandril points in said clamping fixture at said two marks.

5. A method as defined in claim 1 or 2, further comprising:
   producing said pilot borehole from said blank after carving said drilling template;
   applying a mark to a surface of said drilling template while carving said drilling template from said blank;
   securely affixing a blank holder to said drilling template;
   removing said drilling template and said blank holder from said fabricating device;
   clamping said drilling template in a clamping fixture, said blank being held in position using a securing device;
   removing said clamping fixture; and
   producing said pilot borehole at said mark using a drilling rig.

6. A method as defined in claim 5, wherein said mark is applied to said surface of said drilling template as an indentation using said fabricating device.

7. A method as defined in claim 6, wherein said clamping fixture comprises two mandril points and two marks are applied to said drilling template at said two penetration points relevant to said pilot borehole, said marked drilling template being clamped in said clamping fixture between said mandril points at said two marks.

8. A method as defined in claim 7, wherein said securing device comprises rubber pads between which said blank or drilling template is clamped.

9. A method as defined in claim 1 or 2, comprising:
producing said pilot borehole prior to carving said drilling template from said blank;
predetermining a penetration point relevant to said pilot borehole axis on an external surface of said 3D blank model by virtual computerization prior to carving said drilling template from said blank;
clamping and scanning said blank in said fabricating device;
applying a mark to said external surface of said blank at said penetration point relevant to said pilot borehole axis;
removing said blank from said fabricating device;
clamping said marked blank using a blank holder in a clamping fixture that is adjustable for tilt and rotation of said blank relative to said clamping fixture, said blank being positioned such that said pilot borehole axis coincides with an axis of a tool in a drilling rig for drilling said pilot borehole; and
drilling said pilot borehole at said mark using said drilling rig.

10. A method as defined in claim 1 or 2, further comprising:
producing said pilot borehole from said blank after carving said drilling template;
predetermining a penetration point relevant to said pilot borehole axis on an external surface of said 3D drilling template by virtual computerization prior to carving said drilling template from said blank;
clamping and scanning said blank in said fabricating device;
applying a mark to a surface of said drilling template at said penetration point while carving said drilling template from said blank;
securely affixing a blank holder to said drilling template;
removing said drilling template and said blank holder from said fabricating device;
clamping said marked drilling template using said blank holder in a clamping fixture that is adjustable for tilt and rotation relative to said clamping fixture, said blank being positioned such that said pilot borehole axis coincides with an axis of a tool in a drilling rig for drilling said pilot borehole; and
drilling said pilot borehole at said mark using said drilling rig.

11. A method as defined in claim 9, wherein said tilt may be set at an angle between 0° and 90° and said rotation may be set at an angle between 0° and 360°.

12. A method as defined in claim 10, wherein said tilt may be set at an angle between 0° and 90° and said rotation may be set at an angle between 0° and 360°.

13. A method as defined in claim 1 or 2, wherein a plurality of marks are applied to said blank or said drilling template using said fabricating device, and each pilot borehole is provided with a distinct number.

* * * * *